Figure 1:
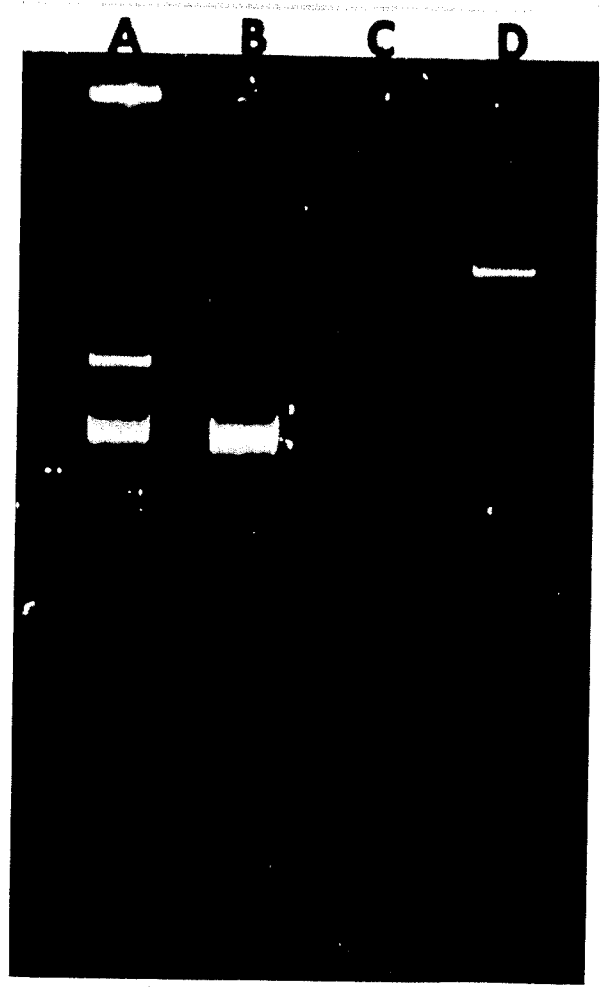

United States Patent [19]

Colaruotolo et al.

[11] Patent Number: 4,477,570

[45] Date of Patent: Oct. 16, 1984

[54] MICROBIAL DEGRADATION OF OBNOXIOUS ORGANIC WASTES INTO INNOCUCOUS MATERIALS

[75] Inventors: Joseph F. Colaruotolo, Grand Island, N.Y.; Ronald H. Olsen, Ann Arbor, Mich.; Peter A. Vandenbergh, Sarasota, Fla.

[73] Assignee: Occidental Chemical Corporation, Niagara Falls, N.Y.

[21] Appl. No.: 305,079

[22] Filed: Sep. 24, 1981

[51] Int. Cl.$^3$ .......................... C12N 1/20; C12N 1/00; C12N 15/00
[52] U.S. Cl. .................................. 435/253; 435/317; 435/172.3; 435/262
[58] Field of Search ............... 435/172, 253, 262, 317, 435/874, 172.1, 172.3; 210/600, 601, 605, 610, 611

[56] References Cited

U.S. PATENT DOCUMENTS

| | | | |
|---|---|---|---|
| 3,779,866 | 12/1973 | Azarowicz | 435/262 |
| 3,813,316 | 5/1974 | Chakrabarty et al. | 435/172 |
| 3,923,360 | 12/1975 | Chakrabarty et al. | 435/874 X |
| 3,979,283 | 9/1976 | Prudom | 435/262 |
| 4,237,224 | 12/1980 | Cohen et al. | 435/68 |
| 4,391,887 | 7/1983 | Baumgarten et al. | 210/610 |

FOREIGN PATENT DOCUMENTS

647339  2/1979  U.S.S.R. .............................. 435/262

OTHER PUBLICATIONS

Evans et al., "Bacterial Metabolism of 2,4-Dichlorophenoxy Aceta", *Biochem. J.*, vol. 122, (1971), pp. 543-551.

Tiedje et al., "2,4-D Metabolism: Pathway of Degradation of Chlorocatechols by Arthrobacten Sp.", *J. Agr. Food Chem.*, vol. 17, No. 5, (1969), pp. 1021-1026.

Hartmann et al., "Metabolism of 3-chloro, 4-chloro and 3,5-dichlorobenzoate by a Pseudomonad", App. & Environ. Microbiol., vol. 37, No. 3, (1979), pp. 421-428.

Schubert, "Toxicity of Organohalogen Compounds to Bacteria and Their Degradability", Fed. Min. for Res. and Tech. Research Report, 03 7123 (1979).

Alexander, "Biotechnology Report Nonbiodegrable and Other Recalcitrant Molecules", Biotech. & Bioengin., vol. 15, (1973), pp. 611-647.

Clarke et al., "Metabolic Pathways and Regulation 1", *Genetics and Biochemistry of Pseudomonas*, John Wiley & Sons, N.Y., (1975), pp. 191-261.

Chatterjee et al., "Plasmid Specifying Total Degradation of 3-Chlorobenzoate by a Modified Ortho Pathway", J. Bact., vol. 146, No. 2, (1981), pp. 639-646.

Vandenbergh et al., "Isolation and Genetic Characterization of Bacteria that Degrade Chloroaromatic Compounds", *App. Environ. Microbiol.*, vol. 42, No. 4, (1981), pp. 737-739.

Royle et al., "Genetic Circularity of the Pseudomonas Aeruginosa PAO Chromosome", J. Bact., vol. 145, No. 1, (1981), pp. 145-155.

Olsen, et al., "RPI Properties and Fertility Inhibition Among P, N, Wand X Incompatibility Group Plasmids", *J. Bact.*, vol. 123, No. 1, (1975), pp. 28-35.

Olsen et al., "Evolution and Utility of a Pseudomonas Aeruginosa Drug Resistance Factor", *J. Bact.*, vol. 125, No. 3, (1976), pp. 837-844.

Kellogg et al., "Plasmid Assisted Molecular Breeding: New Technique for Enhanced Biodegradation of Persistant Toxic Chemicals", Science, vol. 214, (1981), pp. 1133-1135.

(List continued on next page.)

*Primary Examiner*—Thomas Wiseman
*Assistant Examiner*—James Martinell
*Attorney, Agent, or Firm*—Peter F. Casella

[57] ABSTRACT

This invention relates to microbial methods and materials useful in the degradation of organic chemicals having toxic and obnoxious characteristics into innocuous materials compatible with the environment and to the process comprising identification, production and utilization of microorganisms for said purposes.

15 Claims, 1 Drawing Figure

OTHER PUBLICATIONS

Chatterjee et al., "Genetic Approaches to the Problems of Toxic Chemical Pollution", Third Cleveland Symposium of Macromolecules: Recombinant DNA (1981).

Chatterjee et al., "Plasmids in Biodegradation of Chlorinated Aromatic Compounds", *Molecular Biology, Pathogenicity and Ecology of Bacterial Plasmids*, (1981), pp. 519-528.

Hansen et al., "Isolation of Large Bacterial Plasmids and Characterization of the P2 Incompatibility Group Plasmids pMG1 and pMG5", *J. Bact.*, vol. 35, No. 1, (1978), pp. 227-238.

Meyers et al., "Simple Agnrose Gel Electrophoretic Method for the Identification and Characterization of Plasmid Deoxyribonucleic Acid", *J. Bact.*, vol. 127, No. 3, (1976), pp. 1529-1537.

Clark et al., "Degradation of Polychlorinated Biphenyls by Mixed Microbial Cultures", *App. & Environ. Microbiol.*, vol. 37, No. 4, (1979), pp. 680-685.

Furukawa et al., "Effect of Chlorine Substitution on the Biodegradability of Polychlorinated Biphenyls", *App. & Environ. Microbiol.*, vol. 35, No. 2, (1978), pp. 223-227.

Shapiro et al., "Perspectives for Genetic Engineering of Hydrocarbon Oxidizing Bacteria", Proceedings of a Symposium held at Brookhaven Nat. Lab., Dec. 7-11, 1980.

Higgins et al., "Biotransformation of Hydrocarbons and Related Compounds by Whole Organism Suspensions of Methane-Grown *Methylosinus trichosporium* OB3b", *Biochem. Biophys. Res. Comm.*, vol. 189, No. 2, (1979), pp. 671-677.

Chakrabarty, "Plasmids in Pseudomonas", *Ann. Rev. Genet.*, vol. 10, (1976), pp. 7-30.

Bourguin et al., "Microbial Degradation of Halogenated Hydrocarbons", Water Chlorination: Environ. Impact Health EFF Proc. Conf. (1978), pp. 253-264.

Gibson et al., "Oxidative Degradation of Aromatic Hydrocarbons by Microorganisms, II. Metabolism of Halogenated Aromatic Hydrocarbons", *Biochemistry*, vol. 7, No. 11, (1968), pp. 3795-3802.

Dorn et al., "Isolation and Characterization of a 3-Chlorobenzoate Degrading Pseudomonad", *Arch. Microbiol.*, vol. 99, (1974), pp. 61-70.

MICROBIAL DEGRADATION OF OBNOXIOUS ORGANIC WASTES INTO INNOCUCOUS MATERIALS

BACKGROUND OF THE INVENTION

The unprecedented growth of the chemical industry since World War II has led to somewhat over 35 million metric tons of mostly toxic waste being generated. Large quantities of synthetic halogenated materials such as dielictric fluids, flame retardants, refrigerants, heat transfer fluids, lubricants, protective coatings, pesticides, including herbicides and insecticides, and many other chemicals and petroleum products useful in agriculture, industry and health care have been manufactured and used to the benefit of mankind. In many cases, these materials and their by-products or residues from their manufacture have been released into the ecosphere and have been accumulated in landfills, the atmosphere, lakes, rivers and streams, as runoff or direct discharge.

Many of the halogenated chemicals employed in these applications in agriculture and industry are toxic and accumulate in animal and plant tissues causing serious discomfort or health problems. Many also persist in the environment because they are not biodegradable because of the inability of natural microflora generally available in the environment to degrade them.

Many methods and techniques have been proposed and used for disposing of and/or treating these chemicals, their by-products, and their wastes in a way which makes them compatible with the environment. In spite of all the effort and money being spent to clean up the ecosphere, the problem persists. Disposing of waste chemicals accumulated from past practices and preventing future accumulation of such noxious materials is of worldwide concern. The continuing manufacture of such chemicals, which have proven to be essential and so important and necessary to agriculture, industry, and health care in the betterment of mankind continues, and so does the piling up of the obnoxious wastes which are non-biodegradable or not disposable into the natural carbon cycle.

BRIEF DESCRIPTION OF THE INVENTION

This invention relates to methods for collecting, making, and using microorganisms capable of dissimilating chemicals such as halogenated organic compounds back into the natural carbon cycle.

In addition, this invention relates to novel plasmids, or unique regions of the bacterial chromosome associated with the degradative activities, their microbiological preparation and to their utility as cloning vehicles in recombinant DNA work especially for the purpose of enhancing the ability of microorganisms to biodegrade obnoxious halogenated organic wastes.

More particularly, this invention relates to bacterial strains or cultures capable of converting chlorinated aromatic compounds into carbon dioxide, water and salt.

Further, this invention relates to the process for microbial degradation of obnoxious organic wastes into innocuous materials which comprises:

1—collecting a sample of material from the site contaminated with the obnoxious chemicals,
2—enriching the microorganisms found living in the sample,
3—separating the strains of microorganisms capable of having different metabolisms for the various chemicals in the sample from the site, from each other,
4—purifying the strains which are capable of biodegrading the chemicals to be disposed of,
5—applying the strain(s) to the locus of the contaminants to be disposed of, and
6—monitoring of removal of the contaminants at the locus of the application.

Still further, this invention relates to the process for improving the biodegradability of the biologically purified cultures of the microorganisms isolated from the locus of the contaminants (the purified bacterial strains) which comprises transforming the purified strains to another strain of bacteria capable of metabolizing a different chemical in the contaminants to be disposed of.

Another process of this invention comprises conjugal mating the purified strains as the genetic doner with a bacterial strain capable of metabolizing a different chemical in the contaminants to be disposed.

Still another process of this invention involves cell fusion whereby two bacteria become one and new combinations of genes are obtained.

Another process of this invention comprises transduction whereby bacterial viruses transduce genetic material from a donor bacteria to a genetic recipient.

THE PRIOR ART

Over the past few decades especially in the last ten years, hundreds of millions of dollars and many years of effort have been spent in trying to clean up the ecosphere. There have been many academic disclosures which describe bacteria which grow on aliphatic, cycloaliphatic, aromatic and polynuclear aromatic compounds. For example, a variety of microorganisms have been isolated that have the capability of efficiently utilizing aromatic organic chemicals as sole carbon sources for growth (e.g. toluenes, phenols, and napthalene). See Clarke, P. H. and Ornston, L. N. (1975) "Metabolic Pathways and Regulations", 1, 191–196 in Clarke, P. H. and Richmond, M. H. (ed.), "Genetics and Biochemistry of Pseudomonas", John Wiley, London. Also see Chakrabarty, A. M., (1976) "Plasmids in Pseudomonas", *Ann. Rev. Genet.* 10:7–30. However, chlorinated compounds are biodegraded very slowly, if at all. See Alexander, M. (1973) "Non-Biodegradable and Other Recalcitrant Molecules", Biotechnology—Bioengineering, 15:611–647. Notwithstanding, microorganisms have been isolated from the environment that are capable of growth on chlorinated aromatic compounds. For example, Chakrabarty, A. M., (1981) Plasmids in Biodegradation of Chlorinated Aromatic Compounds, Molecular Biology, Pathogenicity, and Ecology of Bacterial Plasmids discloses bacteria which utilize haloaromatic compounds and the degradative pathways of intermediates involved. Several other publications deal with the microbiodegradation of halogenated hydrocarbons. For example, Bourquin, A. W. and Gibson, D. T. (1978) "Microbial Degradation of Halogenated Hydrocarbons; Water Chlorination Environmental Impact and Health Effects", 2, 253–264 disclose various microorganisms such as: Aspergillus sp., Achromobacter sp., Arthrobacter sp. and Clostridium sp., as useful for dehalogenation of various substrates such as 2-chlorophenoxyacetate, 2,4-dichlorophenol, 3-chlorobenzoate, hexachlorocyclohexane, and 4-chlorobenzoate. Gibson, D. T., Koch, J. R., Schuld, C. L. and Kallio, R. E. (1968)—Biochemistry, 7 No. 11 3795–3802 in their paper on Oxidative Degradation of Aromatic Hydrocarbons by Microorganisms including the Metabolism of Halogenated Aromatic Hydrocarbons disclosed *Pseudomonas putida* as useful in the degradation of toluene and chlorinated compounds such as halobenzenes and p-chlorotoluene and state that the presence of halogen atoms greatly reduces the biodegradability of aromatic compounds. They also disclose that microorganisms have also been isolated that have the capability to co-metabolize a chlorinated aromatic chemical growth on its nonchlorinated analog. For example, the conversion of chlorotoluene to chlorocatechol during growth of *Pseudomonas putida* on toluene has been demonstrated. This organism would not further metabolize the chlorocatechol, rather it is known that other microorganisms possess the ability to metabolize chlorocatechols, see Dorn, E. M., Hellwig and Reineke, W. and Knackumss, H. J. (1974), "Isolation and Characterization of a 3-Chlorobenzoate Degrading Pseudomonas", Arch. Microbiology 99, 61–70 and also see Evans, W. C.; Smith, B. S. W.; Fernley, H. N.; and Davies, J. I. (1971), "Bacterial Metabolism of 2,4 Dichlorophenoxy Acetate, Biochem J., 122, 543–551. Chlorocatechol is known to be an intermediate in many of the metabolic pathways for utilization of chlorinated aromatic compounds. The chlorocatechol is further metabolized with the subsequent removal of chlorine. See Tiedje, J. M.; Duxbury, J. M.; Alexander, M. and Dawson, J. E. (1969), 2,4 D Co-metabolism: Pathway of Degradation of Chlorocatechols by Arthrobacter, J. Agr. Food Chem, 17, 1021–1026. Hartmann, J., Reineke, W., Knackmuss, H. J., (1979) Applied & Environmental Microbiology: 37, No. 3, 421–428 show a species of Pseudomonas identified as sp. WR912 capable of degrading chlorobenzoic acids. Shubert, R., (1979) Fed. Ministry for Research and Technology, Goethe University, Frankfurt, W. Germany in his paper on Toxicity of Organohalogen Compounds, discloses the Minimal Inhibitory Concentrations preventing growth of various bacteria including a *Pseudomonas cepacia* in various chlorinated compounds including chlorotoluene. Clark, R. R., Chian, E. S. K. and Griffin, R. A., (1979) Applied & Environmental Microbiology 680–685 discuss the Degradation of Polychlorinated Biphenyls by Mixed Microbial Cultures and conclude the higher the chlorine content the more difficult it is to biodegrade. Furukawa, K. Tonomura, K. and Kamibayashi, A., (1978) Applied & Environmental Microbiology, 35 No. 2, 223–227, "Effect of Chlorine Substitution on the Biodegradability of Polychlorinated Biphenyls", show the effect of chlorine substitution on biodegradability of polychlorinated biphenyls. Shapiro, J. A. et al, (1980) in "Perspectives for Genetic Engineering of Hydrocarbon Oxidizing Bacteria" published in Trends in the Biology of Fermentation for Fuels and Chemicals, Brookhaven National Laboratory, December 7–11, 1980 gives perspectives for genetic engineering of hydrocarbon oxidizing bacteria. It has been widely believed that dechlorination of chlorinated aromatic compounds only occurred after dearomization of the aromatic ring. For example, after meta fision of the ring, the ability of whole cell suspension of *Methylosinus trichosporium* to dechlorinate chlorotoluenes without ring cleavage has been demonstrated. See Higgins, I. J. Hammond, R. C., Sariaslani, F. S., Best, D., Davies, M. M., Tryhorne, S. C. and Taylor, M. F. (1979), "Biotransformation of Hydrocarbons and Related Compounds by Whole Organisms Suspension of Methane-Grown *Methylosinus trichosporium* OB36", Biochem. Biophys. Res. Commun., 89, 671–677. Products of the reaction included benzyl alcohol, benzyl epoxide and methyl benzyl alcohol. Dechlorinating ability of *M. trichosporium* was attributed to the activity of the methane monooxygenase system of the organism. These are the more pertinent examples of the scientific publications available as background on the Microbial degradation of organic compounds.

Notwithstanding all the effort, as represented by the scientific publications in this area of technology, there has been no practical application of these techologies in cleaning up the ecosphere. Furthermore, it has been suggested that because halogenated compounds are not generally found in nature, microorganisms have not evolved which possess efficient enzyme systems or genes which express themselves for the degradation of such chemicals; see Chatterjee, D. K., Kellogg, S. T., Furukawa, K., Kilbane, J. J., Chakrabarty, A. M., "Genetic Approaches to the Problems of Toxic Chemical Pollution", Third Cleveland Symposium on Macromolecules, 1981. Chakrabarty disclosed a technique for artificially inducing the biodegradability of 2,4,5 trichlorophenyl acetic acid (2,4,5 T) by gradually exposing bacteria to increased concentrations of the chemical over the course of about one year; see Chatterjee, D. K., Kellog, S. T., Eatkins, D. R. and Chakrabarty, A. M. in Levy, S., Clowes, R. and Koenig, E. (Eds.), "Molecular Biology, Pathogenicity and Ecology of Bacterial Plasmids", Plenum Publishing Corp., N.Y., 1981, pp. 519–528.

Contrary to these teachings, and much to our surprise, we have found that microorganisms present in the locus of concentrated deposits of halo-organic chemicals have not only managed to stay alive but have adapted themselves to grow and multiply on the halo-organic e.g., chlorinated hydrocarbons in the landfill as their sole source of carbon and energy.

Although we do not wish to be confined to any theory as to why this phenomena exists, we offer the following possibilities, provided they are not construed as limiting our invention and discoveries, except as expressly contained in the appended claims.

Prior to chemical wastes being accumulated in a given landfill the soil and surrounding environment was populated with bacteria that used the normal hydrocarbon material in the soil as their source of carbon and energy. As the obnoxious chlorinated organics and other wastes were deposited on them, all but the strongest were killed off. Per Charles Darwin's theory of survival of the fittest including the process of evolution which includes isolation, speciation, mutation and other processes and mechanisms, conjugation into other bacteria whether of the same strain, species, genera or different involved in the process of natural selection certain of these bacteria adapted their metabolisms to break the carbon-chlorine bond causing the formation or more easily metabolized materials, e.g. catechols or further metabolized derivative compounds, haloaliphatic compounds, which are more in line with the substrates the bacteria have been accustomed to metabolizing.

Another possibility is that the bacteria in the soil always possessed genes in their DNA which were capable of metabolizing chlorinated organics. These genes may have been active and expressed in the ancestors of the organisms when salt and chlorine may have been more concentrated and abundant in their sites. But in recent times, the bacteria never had to use them, i.e., such genes were not expressed because there were easier metabolized carbon material on their sites for them to thrive on. This theory supports the fact that the low concentrations of chlorinated organics in the ecosphere due to pesticide applications are not concentrated enough to cause the bacteria to adapt to metabolizing them, thus, the persistance of these chemicals in the soil and ecosphere and their nonbiodegradability.

No matter what the theory, we have found that bacteria capable of biodegrading a waste are created at the locus of the waste when there is a significant concentration of the waste to the exclusion of other sources of carbon for the bacteria to feed on and when enough time has elapsed thereby allowing for the mutations in the bacteria which allow for their biodegradation to be continuously expressed from one generation to the next.

DESCRIPTION OF THE INVENTION

Samples of soil and leachate were recently obtained from a landfill site of the Hooker Chemical and Plastics Corp. in Niagara Falls, N.Y. which had been used for disposal of chlorinated organic wastes during the period 1955 to 1975. These samples were utilized in enrichment experiments and were found to contain microorganisms that were able to dissimilate 2-chlorotoluene, 3-chlorotoluene, 2,6-dichlorotoluene, 3,4-dichlorotoluene, 2,4-dichlorobenzoate and 3,4-dichlorobenzoate as sole carbon and energy sources for growth. The identity of the bacteria that degrade the chloroaromatic compounds was established as Pseudomonas species and are specifically designated respectively as follows HCI(2CT), HCIV(3CT), HCV(2,6-DCT)-2, HCV(3,4-DCT)-5, HCV(2,4-DCB), HCV(3,4-DCB), HCV(2,6-DCT)-3, HCV(3,4-DCT)-7, HCV(2,6-DCT). HCV (2,6-DCT)-2, and HCV(2,6-DCT)-3 have been further identified as *Pseudomonas cepacia* and all strains will be identified as *Pseudomonas cepacia* var., niagarous.

The processes of sampling, enrichment, isolation, separation, purification and application employed will be given in the examples which follow. Further disclosure and identification of the bacteria follows.

Cultures of the Pseudomonas species have been deposited with the American Type Culture Collection, 12301 Parkway Drive, Rockville, Md. 20852. The microorganisms have been given the following identifying ATCC numbers.

| Strain Designation | ATCC Number |
|---|---|
| HCI(2 CT) | ATCC-31945 |
| HCIV(3 CT) | ATCC-31941 |
| HCV(2,4 DCB) | ATCC-31942 |
| HCV(3,4 DCB) | ATCC-31940 |
| HCV(2,6 DCT)-2 | ATCC-31943 |
| HCV(2,6 DCT)-3 | ATCC-31944 |
| HCV(3,4 DCT)-5 | ATCC-31939 |

The organism shall be made permanently available to the public in accordance with the Apr. 29th, 1971 Commissioner's notice appearing at 8860G638.

THE FIGURE AND THE TABLES

FIG. I shows the Agarose gel electrophoresis analysis of cesium chloride ethidium bromide purified DNA preparations derived from parental recipient transformant and transconjugant strains as will be discussed later in the examples.

Table I gives the Morphological, Cultural and Physiological properties of a specific *Pseudomonas cepacia* var., niagarous HCV (2,6 DCT)-2. The physiological properties in Table I were determined by the API 20E System which is a standardized miniaturized version of conventional procedures for the identification of Enterobacteriaceae and other Gram-negative bacteria. Analytab Products, 200 Express Street, Plainview, N.Y. 11803.

The microorganism *Pseudomonas cepacia* is a Gram negative bacterium having the following characteristics: rods which are very short and plump with the following usual dimensions—0.5 μm by 1.5-4 μm.

Table II gives the hydrocarbon utilization at 300 ppm of some of the *Pseudomonas cepacia* var., niagarous of this invention. After primary isolation and purification utilizing one substrate as the carbon source, the microorganisms were tested for growth on other substrates at 300 and 1000 ppm. The growth was monitored on solid media vs. nutrient agar as control.

Table III gives the hydrocarbon utilization of the *Pseudomonas cepacia* var., niagarous of 1000 ppm.

Table IV gives the antibiotic resistances of some of the *Pseudomonas cepecia* var., niagarous.

Table V gives the substrate utilization profile for transformants and conjugants given in Example I for PAO 2178 (pRO 63) which identification is in accordance with the National Plasmid Registry Stanford University Medical School, Palo Alto, Calif.

TABLE I

MORPHOLOGICAL/CULTURAL/PHYSIOLOGICAL PROPERTIES

PSEUDOMONAS CEPACIA
(STRAIN HCV (2,6 DCT)-2 ATCC-31943

A. Morphological Properties
  1. Small rods
  2. Gram (−) negative
  3. No spores
B. Cultural Properties
  1. Growth at ambient to 42° C.
  2. Growth on mineral salts and carbon source
  3. Yellow pigment @37° C. on nutrient media
  4. Glossy smooth, entire colonies on nutrient media
C. Physiological Properties
  1. -galactosides + (hydrol of ONPG)
  2. Arginine decarboxylase (−)
  3. Lysine decarboxylase (−)
  4. Citrate (+)
  5. $H_2S$ produced from Thiosulfate (+)
  6. Ammonia not produced from urea (−)
  7. Gelatinase (+)
  8. Carbohydrate utilization
     (a) Inositol (−)
     (b) Rhamnose (−)
     (c) Melibiose (−)
     (d) Amygdalose (−)
     (e) Arabinose (−)
     (f) Glucose (+)
     (g) Mannitol (+)
     (h) Sorbitol (+)
     (i) Sucrose (+)
  9. Oxidase (+)
  10. Nitrate reduced to nitrite (+)

TABLE II

HYDROCARBON UTILIZATION AT 300 PPM SUBSTRATE CONCENTRATION*

| Compound | HCI 2CT | HCIV 3CT | HCV 2,4DCB | HCV 3,4DCB | HCV 3,4DCT | HCV 2,6DCT-2 |
|---|---|---|---|---|---|---|
| 2 Chlorotoluene | 2.3 | 2.3 | 2.3 | 2.3 | 2.3 | 2.3 |
| 3 Chlorotoluene | 3 | 3 | 3 | 3 | 3 | 3 |
| 3,4 Dichlorotoluene | 3 | 3 | 3 | 3 | 3 | 3 |
| 2,6 Dichlorotoluene | 2.3 | 2 | 2.3 | 2.3 | 2.3 | 2 |
| Benzoate | 4 | 0 | 4 | 4 | 4 | 4 |
| 4 Chlorobenzoate | 2.3 | 1.7 | 2 | 2 | 2 | 2.3 |
| 2,4 Dichlorobenzoate | 3 | 2 | 3 | 3 | 3 | 3 |
| 2,4 D | 3 | 2 | 3 | 3 | 3 | 3 |
| 2,4,5 T | 2 | 2.5 | 2 | 2 | 1 | 2 |

*Growth on substrate vs. nutrient agar scored from 1 to 4 with 4 designating highest growth rate.

TABLE III

HYDROCARBON UTILIZATION AT 1000 PPM SUBSTRATE CONCENTRATION

| Compound | HCI 2CT | HCIV 3CT | HCV 2,4DCB | HCV 3,4DCB | HCV 3,4DCT | HCV 2,6DCT-2 |
|---|---|---|---|---|---|---|
| 2 Chlorotoluene | 3 | 2 | 3 | 3 | 3 | 2.5 |
| 3 Chlorotoluene | 3 | 2 | 3 | 3 | 3 | 2.5 |
| 3,4 Dichlorotoluene | 3 | 2 | 3 | 3 | 3 | 2.5 |
| 2,6 Dichlorotoluene | 2.5 | 2 | 3 | 3 | 3 | 2 |
| Benzoate | 4 | 0 | 4 | 4 | 4 | 4 |
| 4 Chlorobenzoate | 3 | 0 | 3 | 3 | 3 | 3 |
| 2,4 Dichlorobenzoate | 4 | 3 | 4 | 4 | 4 | 4 |
| 2,4 D | 3 | 1.5 | 3 | 3 | 3 | 3 |
| 2,4,5 T | 2.5 | 1 | 2.5 | 2.5 | 2.5 | 2.5 |

TABLE IV

ANTIBIOTIC SUSCEPTIBILITY*
(Numbers in parentheses are concentrations in millicentigrams)

| | TETRACYCLINE (30) | NALIDIXIC ACID (30) | AMPICILLIN (10) | GENTAMICIN (10) | PENICILLIN (15) | ERYTHROMYCIN (50) |
|---|---|---|---|---|---|---|
| HCI 2CT | R | I | R | S | R | R |
| HCIV 3CT | S | S | R | S | R | R |
| HCV 2,4DCB | R | R | R | S | R | R |
| HCV 3,4DCB | R | R | R | S | R | R |
| HCV 3,4DCT | I | S | R | S | R | R |
| HCV 2,6DCT-2 | S | S | R | S | R | R |

| | CARBENICILLIN (50) | CARBENICILLIN (100) | CHLORAMPHENICIL (30) | COLISTIN (10) | STREPTOMYCIN (10) | KANAKMYCIN (30) | AUREOMYCIN |
|---|---|---|---|---|---|---|---|
| HCI 2CT | NA | R | R | S | S | S | NA |
| HCIV 3CT | R | R | I | S | R | S | S |
| HCV 2,4DCB | R | R | R | S | I | S | S |
| HCV 3,4DCB | R | R | R | S | I | S | S |
| HCV 3,4DCT | R | R | R | S | I | S | S |
| HCV 2,6DCT-2 | S | S | S | S | I | I | S |

*Antibiotic Susceptibility scored by the method of Kerby and Bauer, Am. J. Clinical Path., 45, 493 (1966).

TABLE V

SUBSTRATE UTILIZATION PROPERTIES OF DERIVED STRAINS

| | | | TRANSFORMANTS | | TRANSCONJUGANSTS | |
|---|---|---|---|---|---|---|
| Compound | PAO 2178 | HCV(2,6 DCT)-2 | PAO 2178(2,6 DCT-2)-1 | PAO 217(2,6 DCT-2)-2 | PAO 2178(2,6 DCT-2)-3 | PAO 2178(2,6 DCT-2)-4 |
| 2 Chlorotoluene | − | + | + | + | + | + |
| 3 Chlorotoluene | − | + | + | + | + | + |
| 4 Chlorotoluene | − | + | + | + | + | + |
| 2,6 Dichlorotoluene | − | + | + | + | + | + |
| 3,4 Dichlorotoluene | − | + | + | + | + | + |
| 2 Chlorobenzoate | − | + | + | + | + | + |
| 3 Chlorobenzoate | − | − | + | + | + | + |
| 4 Chlorobenzoate | − | − | + | + | + | + |
| 2,4 Dichlorobenzoate | − | + | + | + | + | + |
| 3,4 Dichlorobenzoate | − | + | + | + | + | + |
| p-Toluic Acid | − | − | + | + | + | + |
| Toluene | − | − | + | + | + | + |

Volatile carbon sources were incorporated directly in the medium as well as in the vapor phase in a sealed container.
+ = Growth
− = No Growth

THE EXAMPLES

The following examples are given to further describe our invention however, they are given for illustrative purposes only and are not included to limit the scope of our invention except as defined in the appended claims.

EXAMPLE I

Collection

Soil samples were collected during the month of May from portions of a landfill site at a depth of above about 8 to 12 inches to the top of the soil in Niagara Falls, N.Y. at a place where there was a high concentration of contaminants and where the odor of halogenated chemicals in the soil was self-evident. The landfill has been used for obnoxious organic wastes including chlorinated organics for a period of over 20 years.

Enrichment

Approximately 1 gram of soil was suspended in 25 ml of minimal salts media of the following composition; contained per liter: 40 ml of $Na_2HPO_4 + KH_2PO_4$ buffer (pH 6.8); 20 ml of Hutner's vitamin-free mineral base and 1.0 g of $(NH_4)_2SO_4$. The medium contained 0.2% of L Tryptophan and 0.05% of Difco (Difco Laboratories, Detroit, Mich.) yeast extract, according to the prior art Lichstein, H. C. and Oginsky, E. L. in Experimental Microbial Physiology, W. H. Freeman & Company (1965). The enrichment culture was statically incubated in shallow culture for 72 hours at 25° C.

Isolation & Purification

After incubation, 0.1 ml of the enrichment broth was spread over the surface of solid minimal salts media with a bent glass rod and the plates incubated at 25° C. The solid media also contained 0.2% of a specific haloaromatic carbon source. Several serial isolations were carried out by removing colonies with a wire loop and streaking over the surface of fresh solid media containing a specific haloaromatic carbon source. In this way purified isolates were obtained.

After primary isolation and purification utilizing one substrate as the carbon source, the microorganisms were then tested on solid media for growth on other chlorotoluenes and chlorobenzoate compounds as shown in Table II and III.

Preparation of DNA

Cells from ATCC 31943 which contain plasmids pRO 4.7, pRO 31, and pRO 54 were grown on the surface of nutrient agar plates overnight at 23° C. The cell crops were removed from the nutrient agar plates washed and resuspended at high density in buffered 25% sucrose (pH 8.0) as described by Hanson and Olsen, J. Bacteriology, 135, 227 (1978). All subsequent mixing was done by slow, gentle inversion. To lyse cells, we added lysozyme and ethylenediaminetetraacetate, and then sodium dodecyl sulphate (SDS) to 4% final concentration. Eight repeated cycles of heat pulse and mixing produced a clear, viscous lysate. DNA was denatured at pH 12.1–12.3 by adding 3M NaOH and mixing for 3 min. at room temperature. Then tris(hydroxymethyl)aminomethane (pH 7.0) ws added to return the pH below 9.0. We added SDS to 4% final concentration, NaCl to 1.0M and mixed by 20 inversions; after 6 hours at 4° C., the salt-precipitated chromosome-membrane complexes were pelleted by centrifugation at 17,000 g (4° C., 30 min.). The supernatant was mixed with polyethylene glycol 6000 to 10% concentration. After 6 hours at 4° C., the tubes were centrifuged at 700 g (4° C., 5 min.). Resuspension of the resulting pellets in 0.15 ml cold buffer gave plasmid-enriched DNA solution. Agarose slab gel electrophoresis, for 3 hours at 100 volts through 0.7% agarose (wt./vol.), was carried out using the method of Meyers (Meyers, J. A., Sanchez, Dr. Elwell, L. P. and Falkow, S., Journal of Bact., 127, 1529 (1978). Each well contained 25 $\mu$l of plasmid-enriched DNA solution mixed with 10 $\mu$l Meyers tracking dye. Gels were stained with ethidium bromide solution and visualized on an ultraviolet transilluminator.

FIG. 1 shows a typical Agarose slab gel electrophoresis which is explained in a later part of the disclosure.

Transformation

A portion (25 ml) of TN broth (tryptone, yeast extract, glycose and salt) was inoculated with cells from a nutrient agar plate grown overnight and incubated at 37° C. in a shaker until the optical density (425 $\mu$m) was 1.0. The mixture was centrifuged cold at 10 rpm for 18 minutes and the cells separated from the supernatant and resuspended in 10 ml of 0.15M $MgCl_2$ and allowed to stand for 5 minutes in ice. The mixture was centrifuged again and resuspended as above and held on ice for 20 minutes. The mixture was centrifuged and resuspended as above a third time and 0.2 ml of the resuspended cells added to prepared DNA (10–50 $\mu$l) in a cold centrifuge tube and held on ice for 60 minutes. Heat pulse was applied for 2 minutes at 37° C. and then chilled. Finally, 0.5 ml TN broth at room temperature was added and the mixture staticly incubated 1–2.5 hours at 37° C.

This recipient strain, PAO 2178, (see Royle, P. L., Matsumoto, H. and Holloway, B. W., J. Bacteriol., 145, 145 (1981) requires methionine and is a catechol-1,2-oxygenase mutant and consequently is unable to degrade and chloroaromatic compounds. However, when PAO 2178 was transformed with CsCl purified plasmid DNA prepared from HCV(2,6-DCT)-2, the ability to utilize 2,6-dichlorotoluene was introduced into PAO 2178 at a frequency of approximately $1.9 \times 10^5$ transformants/$\mu$g DNA. Such transformants were able to metabolize all of the chlorotoluene and chlorobenzoate compounds examined, unlike the genetic doner, HCV(2,6 DCT), which did not utilize 3-chlorobenzoate or 4-chlorobenzoate. The substrate utilization profile for the transformants, designated PAO 2178(2,6-DCT-2)-1 and -2, and is also identified herein as PAO 2178(pRO 63), said identification being in accordance with the National Plasmid Registry Stanford University Medical School is shown in Table V. However, this and other transformants (not shown) still required methionine for growth and were unable to utilize benzoate.

Conjugation

Conjugal mating experiments were done using PAO 2178 as the recipient bacterial strain. Strain PAO 2178 was a mutant of $PAO1_c$ (ATCC 15692) as described by Royle, Matsumoto and Holloway. Minimal salts medium and complex medium were prepared as described by Olsen. R. H. and Hansen, J., J. Bacteriol., 123, 28 (1975) and J. Bacteriol., 125, 837 (1976). When nutritional selection against auxotrophic donors was done, amino acid requirements were satisfied by the addition of these components to a final concentration of 20 μg/ml.

All matings were done in TN broth medium. For this, TN broth medium was inoculated with overnight growth from TN agar. These broth cultures were incubated for 3 hours with agitation at 37° C. Inoculation was adjusted to result in approximately $10^8$ cells per ml of TN broth culture after 3 hours of growth. Donor and recipient cells were mixed 1:1 and incubated at 37° C. for 2 hours. Mating mixtures were centrifuged at ambient temperature, and cell pellets were suspended to 1/10 the original volume of 0.01M phosphate buffer (pH 7.0). Cell suspensions were diluted and plated onto mineral salts medium supplemented with the nutrients is specified by the recipient and a haloaromatic compound whose utilization required by the donor plasmid. Plates were incubated for 48 hours at 23° C. Transconjugants were purified by picking colonies into liquid suspension, followed by streaking out for single-colony isolation on solid medium identical to that used for their primary isolation.

The transconjugants obtained were able to metabolize all of the chlorotoluene and chlorobenzoate compounds examined, as was the case for the genetic donor in these conjugation experiments, HCV(2,6-DCT)-2. In addition, they also utilized 3- and 4-chlorobenzoate, compounds not utilized by the doner. The substrate utilization profile for these transconjugants, designated PAO 2178(2,6-DCT-2)-3 and -4 is shown in Table V.

Plasmid DNA was extracted from HCV(2,6-DCT)-2 and a transformant and a transconjugant derived from HCV(2,6-DCT)-2, as described earlier. These DNA preparations were purified in cesium chloride-ethidium bromide gradients and subjected to slab agarose gel electrophoresis. In FIG. 1, file A, plasmid DNA from the parental strain, HCV(2,6-DCT)-2, is shown and it contained plasmids of 4.7, 31 and 54 Mdaltons in molecular size (plasmid size was determined previously using appropriate standards). File B contains the recipient strain PAO 2178. The results in File B demonstrates that the recipient strain does not harbor resident plasmids. File C, shows plasmid DNA extracted from a transformant, strain PAO 2178 (2,6-DCT-2)-1. File D, shows plasmid DNA from a transconjugant strain PAO 2178 (2,6-DCT-2)-3. As shown in files C and D, the plasmid band from either the transformant or transconjugant is approximately 63 Mdaltons in molecular size.

The molecular sizes of plasmids from either transconjugant or transformant strains were similar but larger than those observed in the donor strain HCV(2,6-DCT)-2. This result was unexpected since two different genetic techniques were utilized to transfer the plasmids to the recipient, PAO 2178. The explanation for this is the occasional random formation of a fusion plasmid in the donor bacterial culture, which contains the 4.7 and 54 Mdalton plasmids present usually independently in a donor bacterium. These fusion plasmids have been uniquely selected in the genetic transfer experiments because one of the donor plasmids contains a replicator functional in strain PAO 2178 and the other donor plasmid component contains a nonfunctional replicator but has the genes which encode for the degradative activities. Therefore, maintenance of the degradative activity, in this strain, requires the maintenance of the replicator contained in the 4.7 Mdalton plasmid.

The PAO 2178 strain acquired the ability to utilize various chloroaromatic compounds through transformation or conjugation with HCV(2,6-DCT)-2. The results demonstrate that PAO 2178 acquired the genes necessary for chloroaromatic compound utilization from a transmissible plasmid. Furthermore, the strains acquired through conjugation or transformation showed the ability to use two compounds not degraded by the donor (i.e., 3-chlorobenzoate and 4-chlorobenzoate). This reflects the supportive metabolism present in PAO 2178 not present in HCV(2,6-DCT)-2 for the complete dissimilation of these compounds.

Application

To approximately a kilo of each three clean soils are added 1 gram of 3,4-dichlorobenzoate, 3-chlorobenzoate and 2,6-dichlorotoluene to produce soil samples contaminated to 1000 ppm. Fifth ml of liquid media culture containing HCV(2,6-DCT)-2 and HCV(3,4 DCB) are added to the soil and the mixture incubated at 25° C. Five gram samples of soil are taken daily and analyzed for the substrate.

Five grams of soil are weighed into a 50 ml erlenmeyer flask containing 10 ml of distilled water. The pH of the soil suspension is adjusted to 4.0 with dilute $H_2SO_4$ and extracted with 3 10 ml portions of methylene chloride. The methylene chloride extracts are transferred to a 50 ml volumetric and made up to volume. The methylene chloride solution is analyzed a 254 μm using a Beckman Lamda 3 UV/VIS spectrometer.

Monitoring the utilization of the chloroaromatic substrates shows that 90% of the chloroaromatic substrates are decomposed within 1 week.

In order that the scope and breadth of the process of our invention for biodegrading the contaminants in the ecosphere back into the natural carbon cycle may be more readily understood, the following additional disclosures are made in connection with it.

EXAMPLE II

A sample of contaminated air is obtained in a standard air bag or filter sampling device. The airborne bacteria in the sample which have adapted themselves to metabolize the organic contaminants in the contaminated air back into the natural carbon cycle are enriched, isolated, purified, identified, and produced substantially in accordance with the procedures given in Example No. 1 on HCV (2,6-DCT-2). In this case, the bacteria are applied to the contaminated air in a closed system by known techniques. By periodic monitoring of samples from the locus of the contaminated air, one will find that there will be a reduction in the density of the contaminants.

EXAMPLE III

Leachate from chemical waste landfill drainage is placed in a 500 gallon glass lined pressure reactor, agitated and heated to a temperature of about 30° C. To this reactor is added 2000 parts per million of each of the Pseudomonas strains isolated as in Example I. After 38 hours, the pressure in the reactor will increase up to about 2 atmospheres. The pressure is released through a valve in the reactor. The vented gases are analyzed and found to be mainly carbon dioxide. The remaining contents in the reactor are analyzed and are found to be carbonated salt-water. The concentrations of the noxious toxic chemicals are reduced.

EXAMPLE IV

A new chemical containing 12 chlorine, 12 carbon and 12 hydrogen atoms is made by the Diels-Alder reaction using the appropriate materials. The chemical is found to be useful in large tonnage industrial applications but its residues and by-products which comprise 25% by weight of the desired product are toxic, obnoxious and not biodegradable simply because this material is a new composition of matter never existant in nature. Accordingly, bacteria have never been given a chance to adapt to biodegrade it. In accordance with this invention, the wastes are disposed of in a landfill known to house bacteria not capable of biodegrading the wastes. Samples of the soil are taken at monthly intervals and after 10 months, a bacteria is isolated capable of biodegrading the waste. These bacteria are enriched in accordance with Example I and produced in large quantity for storage. The chemical process equipment in the manufacturing plant for the new composition of matter is adapted to contain an add-on reactor along the lines given in Example III, so that the by-product and effluent streams may be treated by the enriched strains of bacteria which have been recovered from the locus of the landfill which are capable of biodegrading the obnoxious wastes in the plant effluents. In this manner, the process is made ecologically safe and less harmful because of the smaller amount of objectional effluents from this chemical process.

In order that this invention may be more readily understood in greater detail, the following guidelines are given using primarily one embodiment of our invention namely, the biodegradation of a long established chemical landfill containing obnoxious halogenated organic chemicals. However, it should be understood that many of these guidelines are useful in other applications such as collecting bacteria from aqueous environments including lake beds, streams and sediments or from the atmosphere.

In accordance with our invention, bacteria are isolated from the soil of the landfill which soil sample is selected in areas of high concentrations of organic chemical contamination. The continued exposure of bacteria to the high concentrations of contaminants in these environments increases the tolerance of such strains to the contaminants by the process of natural selection and adaptation to the point where over the course of time only strains of bacteria or microbes which can survive such an environment are present. Thus, we employ naturally mutated bacteria which have adapted to live on the chlorinated hydrocarbons as their sole source of carbon and energy as the starting material in our process. It is a further purpose of this invention to provide a process for maintaining and controlling the natural process of selection to produce bacteria with the specialized and desirable waste disposal capabilities. We have found that when our new strains of bacteria are inoculated or otherwise reintroduced to the contaminated environment, particularly if their favorite substrates are either absent or only present in low concentration, they multiply rapidly by metabolizing the halogenated organics to carbon dioxide, water and salt. On the other hand, if the new strains of bacteria are applied to a low concentration contaminated environment containing more favorite substrates, then their ability to biodegrade the chlorinated organics is reduced, if not terminated, or rendered latent or impotent; thus they revert to type unless continually forced to use the waste contaminants as their source of carbon. Employing more favored substrates is one way of controlling the population or even the existance of the bacteria in the location it is used in. Other methods of controlling or destroying the bacteria, if their growth and population exceed the desired limit is to use a non-resistant antibiotic or other biocide.

The collecting of the sample to be enriched in accordance with our invention should be made at a site containing a high concentration of contaminants whether it be in the soil, water or air. The age of locus of contaminated area should be old enough to have allowed for many generations of bacteria to grow so that the bacteria have developed genetically the ability to utilize and degrade the contaminant.

Since the disposal of chemicals in landfills usually was done on a chronological basis and because similar chemicals were usually placed in the same location in the landfill, it may become necessary to take samples of the soil in the landfill from various areas in order to find the microorganisms or bacteria capable of degrading the various chemicals in the landfill. For example, if the northeast quadrant of the landfill was filled with residues and wastes resulting from 2,4,5 T (2,4,5 Trichlorophenol), and, if the southwest quadrant was filled with residues and wastes from the manufacture of chlorotoluenes, then samples of soil from each quadrant (or other measure of the landfill) should be obtained and processed in accordance with this invention, in order to find the best variety in microorganisms or bacteria capable of being upgraded and enhanced, for application in the degradation of the wastes and residues.

Another factor that is important to consider in sampling from the landfill is whether or not the landfill has been "seasoned", that is, has gone through the four seasons of a year so that the microorganisms or bacteria had mutated in a way that allows them to degrade the chemical and other wastes and is also adapted to survive the vigorous temperature and other conditions caused by the extremes of summer heat and winter cold. This is especially important in the northern climates such as in Niagara Falls, N.Y. where temperatures in the summertime can reach 100° F., and in the wintertime below $-30°$ F., and snowfall can exceed 144 or more inches in one winter season. Thus, the atmospheric, weather and other related conditions surrounding the environment of the landfill should be taken into consideration when sampling for bacteria.

Still another factor that should be considered is the depth of soil one should go to, in extracting the samples. Since the microorganisms or bacteria of this invention are aerobic, best strains which are useful in this invention are obtained from the top layer perhaps 8–12 inches deep of the landfill. This is not to preclude sampling for microorganisms or bacteria at depths in the landfill greater than 8–12 inches. For example, soil conditions and composition will effect permeation of air to greater depths. In addition, anaerobic bacteria can be found at still greater depths. There are known landfills which have exceeded 50 ft in depth. Accordingly, sampling at such depths for microorganisms and bacteria are embraced within the concepts of this invention.

Any one of a number of techniques may be used to enrich the bacterial strains in accordance with our invention. For example, instead of the procedure used in Example I, one may employ standard minimal nutrient media and an appropriate carbon source such as given in Hartmann, J., Reineke, W., and Knackmuss, N. J., Applied and Environmental Microbiology, 37, 421 (1979).

The separation, isolation and purification may be done by any one or combinations of the following techniques. The standard microbiological procedure of serial dilution can be applied to enriched mixtures of bacteria to separate, isolate and purify the strains in the enrichment media. Other techniques such as repeated plating on non-inhibitory media and single cell isolations can be used.

Bacteria isolated and described in this way may in some instances serve as a source of critical genetic information for haloaromatic compound degradation that may be acquired by yet other bacteria by any one of or a combination of genetic processes utilized by bacteria for the formation of genetic hybrids. These genetic processes include conjugation and transformation as described herein and also the genetic process of transduction. Bacterial transduction is characterized by the transport of genes from a doner bacterium to a recipient bacterium by viruses grown on the doner and later infecting the recipient bacterium. Still another process called cell fusion may be utilized for genetic exchange by which environmental conditions are established which cause two bactrial cells, a doner and a recipient, to become one cell with common genetic material and cellular cytoplasm. The daughter cells produced when these fused cells reproduce now contain genes representative of both participants in the initial cell fusion.

Various other methods of applying the bacteria to the contaminants to be disposed of may be used. For example, the microorganisms isolated as in Example I are injected along with nutrient media and oxygen into chemical waste landfill. The organisms utilize the waste stored in the landfill as sole source of carbon and energy thus destroying the contents of the landfill.

Soil contaminated by a chemical spill is inoculated with microorganisms isolated as in Example I and the soil subsequently cultivated to oxygenate the soil. Cultivation continues for about 1 week until the chemical residue is reduced to nonhazardous levels.

Another mode of application involves employing bacterial strains or cultures produced in accordance with this invention which have been collected from a room housing a chemical plant for manufacture of chlorinated hydrocarbons, having several parts per million of chlorinated contaminants in the air. The bacterial strains and cultures made in accordance with this invention are desposited on an air filter system and the contaminated air from the plant room circulated through the filter system to produce air less contaminated with the chlorinated materials.

The work done herein was all done in conformity with physical and biological containment requirements specified in the Guidelines published by the National Institute of Health, Washington, D.C. United States of America.

Although our invention has been described using specific examples and certain preferred embodiments thereof, we do not intend that our invention be limited in scope except as expressly defined in the appended claims.

We claim:

1. A biologically pure culture of *Pseudomonas cepacia* var., niagarous selected from the group consisting of ATCC 31945, ATCC 31941, ATCC 31942, ATCC 31940, ATCC 31943, ATCC 31944, ATCC 31939 and mutants thereof useful in decomposing obnoxious halogenated organic wastes to innocuous materials.

2. A microorganism in accordance with claim 1 wherein the *Pseudomonas cepacia* var., niagarous is ATCC 31945.

3. A microorganism in accordance with claim 1 wherein the *Pseudomonas cepacia* var., niagarous is ATCC 31941.

4. A microorganism in accordance with claim 1 wherein the *Pseudomonas cepacia* var., niagarous is ATCC 31942.

5. A microorganism in accordance with claim 1 wherein the *Pseudomonas cepacia* var., niagarous is ATCC 31940.

6. A microorganism in accordance with claim 1 wherein the *Pseudomonas cepacia* var., niagarous is ATCC 31943.

7. A microorganism in accordance with claim 1 wherein the *Pseudomonas cepacia* var., niagarous is ATCC 31944.

8. A microorganism in accordance with claim 1 wherein the *Pseudomonas cepacia* var., niagarous is ATCC 31939.

9. A microorganism host cell of the genus Pseudomonas being an artifically induced mutant transformed with plasmids capable of metabolizing a plurality of different halogenated organic compounds and having the further identifying characteristics of *Pseudomonas cepacia* var., niagarous useful in decomposing halogen containing organic wastes to innocuous materials.

10. A microorganism in accordance with claim 9 having the further identifying characteristics of PAO 2178 (pRO 63), a mutant of $PAOl_c$ (ATCC 15692) and unable to metabolize catechol.

11. A biologically pure hybrid plasmid consisting essentially of pRO 4.7 (having a molecular weight of approximately 4.7 megadaltons), pRO 31 (having a molecular weight of approximately 31 megadaltons), and pRO 54 (having a molecular weight of approximately 54 megadaltons), said pure hybrid plasmid having the further identifying characteristic of being capable of replicating the ability to express the degradation of halogenated organic compounds.

12. A biologically pure plasmid selected from the group consisting of pRO 4.7, pRO 31 and pRO 54 contained in a *Pseudomonas cepacia* var., niagarous selected from the group consisting of ATCC 31945, ATCC 31941, ATCC 31942, ATCC 31940, ATCC 31943, ATCC 31944, ATCC 31939 and mutants thereof, having utility in decomposing obnoxious halogenated organic wastes to innocuous materials, characterized by having a molecular weight of between 4.7 and 54 megadaltons and being capable of fusing with other plasmids of higher molecular weight.

13. The plasmid in accordance with claim 12, namely pRO 4.7 and being stored in ATCC 31943.

14. The plasmid in accordance with claim 12, namely pRO 31 and being stored in ATCC 31943.

15. The plasmid in accordance with claim 12, namely pRO 54 and being stored in ATCC 31943.

* * * * *